United States Patent [19]

Doczi

[11] 3,991,181

[45] Nov. 9, 1976

[54] INJECTABLE STROMA FREE HEMOGLOBIN SOLUTION AND ITS METHOD OF MANUFACTURE

[75] Inventor: John Doczi, Morristown, N.J.

[73] Assignee: Warner-Lambert Company, Morris Plains, N.J.

[22] Filed: June 18, 1975

[21] Appl. No.: 587,945

[52] U.S. Cl. .............................................. 424/101
[51] Int. Cl.² ........................................ A61K 35/14
[58] Field of Search ...................................... 424/101

[56] References Cited

UNITED STATES PATENTS

| | | | |
|---|---|---|---|
| 2,527,210 | 10/1950 | Bower | 424/101 |
| 3,864,478 | 2/1975 | Bonhard | 424/101 |

*Primary Examiner*—Sam Rosen
*Attorney, Agent, or Firm*—Albert H. Graddis; Frank S. Chow; George M. Yahwak

[57] ABSTRACT

The preparation of a stroma-free hemoglobin free of plasma proteins and useful as a plasma extender is disclosed.

5 Claims, No Drawings

INJECTABLE STROMA FREE HEMOGLOBIN SOLUTION AND ITS METHOD OF MANUFACTURE

The ideal therapy for the management of acute hemorrhage is the immediate transfusion of whole blood or pooled plasma. However, whole blood requires typing and crossmatching to avoid incompatible blood transfusion reactions, while viral transmission and short supply are limiting factors common to both whole blood and plasma. For these reasons, other non-toxic and non-reactive materials have been studied for use as plasma substitutes. Among these substitutes are acacia, gum arabic, methyl cellulose, pectin, dextrane, gelatin, bovine serum albumin, PVP, and starch. Many of these materials, however, were found to produce histamine release reactions, hemostatic defects and clumping of the blood elements which often restricted their use. Furthermore, although all are effective to some extent as plasma expanders, they cannot carry oxygen; whole blood remains the ideal for hemorrhagic management.

Hemoglobin solutions have also been used in hemorrhagic shock, since in addition to its osmotic activity hemoglobin can carry and exchange oxygen, and it also does not have the disadvantages of requiring cross matching and typing. Extensive clinical use of hemoglobin solutions have been limited, however, since they interfere with renal function, and produce other toxic effects.

Rabiner, reporting in the Journal of Experimental Medicine for December 1967, postulated that renal damage following administration of a hemoglobin solution could be due to the coagulant activity of red blood cell stromal contaminants and that a stroma free hemoglobin solution would therefore not have deleterious effects on renal function.

The present invention provides a method for obtaining a stroma free hemoglobin solution which substantially overcomes the disadvantages of the known hemoglobin compositions. Essentially, this method is outlined as follows:

Red blood cells are separated by centrifugation from outdated whole human blood and washed by a continuous method with specified volumes of 1.6% and 0.8% sodium chloride solutions. The washed red blood cells are hemolyzed by the addition of phosphate buffer to obtain a hemolysate containing approximately 6.85% hemoglobin. After standing for one hour, the stroma is removed by filtration and the filtrate dialyzed against a solution containing 50 mEq/L sodium bicarbonate in order to reduce the potassium concentration and adjust the pH to normal plasma levels. The calcium, magnesium, sodium, potassium, and chloride ion concentration of the dialyzed solution are determined and adjusted to normal plasma values by the addition of calculated amounts of the appropriate salts. The adjusted solution is passed through a "filter-stack" consisting of a series of membranes with porosities in the range of 1.2 to 0.22 μm. The sterilized filtrate is finally filled into standard containers used for plasma collection.

In order to assure maintenance of sterility and non-pyrogenicity of the finished blood, certain procedures must obviously be maintained: aseptic techniques must be used throughout the manufacture; all equipment, glassware and reagents must be sterilized by steam, ethylene oxide, or dry sterilizations the temperature of the product must be maintained during each manufacturing step at between 2 to 10, preferably 2° to 5° C.

The hemoglobin solution of this invention is prepared from units of outdated human whole blood which have been stored unopened and under proper refrigeration for a short period of time, preferably not longer than three weeks after their date of expiration, and have never been entered after collection. Each unit should meet the standard criteria for in vivo use to assure the absence of sickle cell hemoglobin and hepatitis B surface antigen.

It was found that the consistent preparation of a high purity hemoglobin product requires that the red blood cells used be thoroughly washed, not only to remove viral contaminants but also to assure the absence of plasma constituents and blood group antigens and that this is facilitated if the cells are derived from donors belonging to the same blood group.

The importance of these criteria was established in a series of experiments carried out on the basis that the solution failed to pass a conventional pyrogenicity test and this occurred with a high degree of frequency with hemoglobin solutions obtained from the blood of donors belonging to different blood group types and when the red blood cells were washed with only 1.5L and 0.6L of 1.6% and 0.8% NaCl solutions, respectively.

These observations suggested that a correlation may possibly exist between the pyrogenic and toxic effects observed. On the one hand, and the composition of the red blood cells (with respect to blood type) and the efficiency of their washing, on the other. In order to explain the basis of such a correlation, one may consider a case when O type red blood cells are pooled with type A or B cells. Since O type blood contains anti-A and anti-B immunoglobulins, insufficiently washed red blood cells from such blood will be contaminated with these specific antibodies. Should such contaminated cells then be pooled with either A or B type red blood cells, hemagglutination will occur which could make further washing and processing of the cells very difficult, if not impossible.

It is also known that in approximately 70% of the population, blood group antigens A and B are not confined to the red blood cells alone, but also as water soluble glycoproteins in the plasma. Incomplete washing of red blood cells derived from such individuals would result in cells contaminated with antigens which could then be carried over into the hemoglobin preparation manufactured from the cells, either in the form of the soluble antigen or as a soluble antigen-antibody complex. Although no definite information is available on the possible untoward physiological effects of such contaminants, their presence in a blood mixture is clearly undeniable and may be responsible for the pyrogenic and toxic reactions observed in the pyrogenicity test failure. Furthermore, the possibility exists that insufficiently washed human red blood cells may yield hemoglobin preparations contaminated with heterophile antibodies which could result in the toxic reaction observed during the pyrogen test.

In view of these circumstances and considerations, experiments were carried out in which the saline wash-liquor stream after its passage through the red blood cells was monitored for gradual disappearance of plasma proteins by immunochemical methods. The approach was, in principle, that cells obtained from a single unit of type O blood were sequentially washed with different volumes of solutions containing sodium chloride in different concentrations. Aliquots of the wash-liquor effluents were collected at predetermined frequent intervals and at the completion of the procedure, the washed red blood cells converted to stroma free hemoglobin solution according to the previous outline. The collected wash-liquor aliquots, a sample of the input blood, and the final hemoglobin product were then tested for the detection of plasma proteins by immunochemical methods.

The results obtained in this series of experiments established that hemoglobin solutions prepared from red blood cells, washed first with 3.5 liters of 1.6% saline and then with 0.5 liters of 0.8% saline are free of all three classes of immunoglobulins (IgG, IgM, and IgA). The use of 1.6% NaCl as the first wash solution appears to be important since washing the cells with 5 liters of 0.9% NaCl solution only, resulted in a hemoglobin solution which was still contaminated with immunoglobulins, even though the wash liquor itself was found to be free of them.

The presence of soluble blood group antigens A and B in the wash liquors of red blood cells and in the hemoglobin solution prepared from the cells can be determined by a method based on hemagglutination inhibition, which can detect these antigens in an amount which would be contained in a 0.02% red blood cell suspension. The test was applied to twenty-one individual stroma free hemoglobin preparations prepared from units of type A blood. Of these, only two gave positive results for contamination with blood group antigen A. Based on the sensitivity of the test and the assumption that normal human blood contains 40% red blood cells, it can be calculated that all the preparations, prepared by the method of this invention and found negative with respect to contamination with blood group antigens, contained in a single dose of hemoglobin solution (250 ml) less than the equivalent of 0.125 ml of whole blood. This amount of a potential blood group antigen contaminant is considered — from the standpoint of clinical significance — to be negligible.

The red blood cell washing procedure according to this invention has the advantage that after it has been applied to each individual unit, the washed cells can be pooled for further processing even if they were derived from blood belonging to different types.

After washing the red blood cells by the procedure discussed, they are then hemolyzed in 5 milli Osmoles (mOsm) pH 7.4 phosphate buffer prepared as follows: 14.6 grams of sodium phosphate dibasic is dissolved in 1 liter of distilled water. 21.4 grams of sodium phosphate monobasic is dissolved in 1 liter of distilled water. The monobasic solution is added to the dibasic solution until a pH of 7.4 is reached, and each ml of the pH 7.4 solution is diluted to 62 mls with distilled water to obtain the desired buffer.

The red blood cell stroma is then removed from the hemolyzed suspension by filtration, preferably through a 0.2 $\mu$m filter membrane using preferably a thin channel type recycling filtration system operating between 30 and 40 psi inlet air pressure. The filtration is continued until at least 75% of the input volume has been collected and the filtration rate drops to a point where further filtration is not practical.

The stroma free hemoglobin solution is then dialyzed against a sodium bicarbonate solution to adjust its pH and to reduce the potassium concentration of the solution. This reduction should be continued until the potassium ion concentration is less than 3.5 mEq/L and the pH adjusted to about 7.2 to about 7.4.

The dialyzed hemolysate is then analyzed for the concentrations of calcium, magnesium, potassium, sodium and chloride ions. The concentration of these ions is then adjusted, if need be, to standard levels by the addition of the appropriate salts; these being calcium chloride, magnesium chloride, potassium chloride, sodium chloride and sodium acetate. The standard levels of electrolytes being the recognized normal blood chemistry levels.

The adjusted hemolysate is then filtered through a stack of filters arranged serially in a sequence such that the incoming solution is filtered first by a pre-filter followed by the 1.2 $\mu$m, 0.8 $\mu$m, 0.45 $\mu$m, and finally the 0.22 $\mu$m membrane. Each filter is separated from the next by a Dacron woven mesh separator. Following this filtration, the hemoglobin solution is ready to be used in the management of acute hemorrhage.

After the intravenous infusion of a hemoglobin solution, prepared according to this invention, the recipients whole blood will contain hemoglobin in different environments, i.e. the hemoglobin in the red blood cells erythrocytic hemoglobin, or EHb and free hemoglobin of this invention dissolved in plasma (extra-erythrocytic hemoglobin, or EEHb). Studies were designed to define the oxygen-transport characteristics of blood after hemodilution with hemoglobin solution prepared according to this invention, these studies aimed at answering the following questions: (1) How well is EEHb oxygenated in the lungs? (2) How does EEHb contribute to the oxygen supply of tissues compared with EHb? (3) Does EEHb interfere with the oxygenation of EHb? Experiments were conducted in five barbiturate-anesthetized dogs with hematocrits between 32 and 40%. Isovolumic-hemodilution was induced by exchange transfusion of blood with equal volumes of hemoglobin solution in steps of 10 ml/kg. Five exchange transfusions were performed; this reduced the hematocrit to approximately 50% of the controls. Fifteen to twenty minutes after each exchange transfusion, arterial and venous blood samples were taken in gas tight syringes and a fraction was used to determine hematocrit, hemoglobin content and oxygen content. The remaining blood sample was used to separate the plasma from the red cell mass under methods which prevented the uptake of atmospheric oxygen by the hemoglobin during the process of separation. The plasma sample was used to measure SHb and the oxygen content of SHb. Using these data arteriovenous oxygen difference and oxygen extraction from SHb and EHb at different levels of hemodilution could be calculated.

Mean control values for hematocrit were 35%; hemoglobin 12 grams %; arterial oxygen content 15.8 ml %. During passage through the systemmic vascular bed, 3.4 ml of arterial oxygen per 100 ml blood (22%) was extracted. This is an expected value for barbiturate anesthetized dogs. After hemodilution, oxygen is carried by both the injected hemoglobin in the plasma (SHb) and the hemoglobin of the red blood cells (EHb). During its passage through the lungs, the red blood cell hemoglobin was 95.9 ± 2.4% and SHb was 98.1 ± 1% saturated with oxygen. There was no significant difference in the oxygenation of either EHb or SHb. Before hemodilution EHb was 98.3 ± 2.9% saturated whereas after hemodilution there was 95.9 ± 4%. Thus, the presence of injected hemoglobin, made in accordance with this invention, in the plasma did not interfere with the oxygenation of red blood cell hemoglobin in the lungs.

After hemodilution, venous blood showed a decrease in the oxygen content while the extraction of oxygen from the blood increased. Hemodilution with infused hemoglobin solution according to this invention caused a decrease in the arterial oxygen content. Compensation for such a decrease in oxygen content can be brought about by increasing cardiac output and/or by increasing the extraction of oxygen from the blood; an increase in cardiac output did not occur but there was an increase in extraction oxygen. At levels of extraction between 20 and 50% only EHb contributes to oxygenation of tissues. At levels higher than 50% extraction, EEHb released its oxygen. SHb contributes about half its oxygen when the EHb is completely deoxygenated. This difference in the oxygen supply to tissues is consistent with the higher affinity of SHb for oxygen ($P_{50}$ equals 12–14 mmHg) as compared to the lower affinity of dog whole blood EHb ($P_{50}$ equals 28 mmHg).

In summary, these studies demonstrated that hemoglobin in plasma was as efficiently oxygenated in the lungs as was red blood cell hemoglobin and that a hemoglobin solution prepared according to this invention did not interfere with the arterial saturation of red blood cell hemoglobin but transports and delivers oxygen to tissues. However, this probably does not occur until extraction of oxygen from red blood cells increases above normal levels since infused hemoglobin releases oxygen only to the more hypoxic tissues when oxygen stores in red cells are well depleted. It is likely therefore that in organs such as the heart, extraction of oxygen from hemoglobin in the plasma occurs.

A series of experiments were performed in barbiturate-anesthetized dogs to characterize the renal excretion patterns of infused hemoglobin. Both ureters were catheterized and urine samples were collected every 10 minutes and blood samples taken every 20 minutes for the duration of the experiment. In four experiments, a saline-load of 10 ml/kg was given to insure adequate urine flow. After a 2 hour control period, a 20 ml/kg exchange transfusion (phlebotomy then exchange) with hemoglobin solution was made and plasma and urine hemoglobins were measured. Spectrophotometric analysis of both urine and plasma samples show the pigment in both samples to be identical giving peaks at 540 and 570 mm. In two experiments plasma and urine levels of infused hemoglobin solution were monitored using a different protocol. These dogs were subjected to a 30 minute interval of hypovolemic stress (blood pressure reduced to 50 mm Hg) after which normovolemia was restored using either the standard 6% (44 ml/kg) or a specially prepared 9% solution (34 ml/kg) of hemoglobin solution. These two dogs were not saline loaded. Urine output increased in all 6 dogs immediately following the administration of hemoglobin and the infused hemoglobin appeared in the urine within 5 to 7 minutes after infusion. There appears to be no latent period in the renal excretion of hemoglobin. Concentrations of hemoglobin in the urine samples varied depending on rate of urine formation i.e., the concentration was high when urine output was low and vice versa. The half life in plasma was determined to be 220 minutes; doubling the plasma concentration of hemoglobin by increasing the volume or concentration of the infused hemoglobin solution did not alter the half life significantly.

I claim:

1. A method for obtaining a stroma free hemoglobin solution which is free of plasma proteins comprising the steps of:
   Pooling a quantity of human blood of one ABO blood grouping;
   Washing the erythrocytes of the pooled blood with a 1.6% sodium chloride solution followed by a washing with a 0.8% sodium chloride solution, wherein the solutions used in this washing are of a sufficient volume to remove immunoglobulins from the erythrocytes;
   Lysing the washed erythrocytes in a 5 mOsm pH 7.4 phosphate buffer;
   Filtering the hemolysate to remove cell stroma;
   Adjusting the potassium ion concentration of the stroma free filtered hemolysate to less than 3.5 mEq/L;
   Adjusting the pH of the hemolysate to a pH of about 7.2 to about 7.4;
   Adjusting the concentrations of calcium, magnesium, potassium, sodium, and chloride ions to standard blood chemistry values by the use of appropriate salts; and
   Filtering the adjusted hemolysate.

2. The method according to claim 1 wherein the temperature in which the method is carried out from about 2° to about 10° C.

3. The method of claim 1 wherein the stroma is removed by filtration through a series of 0.2 micron filter membranes.

4. A stromal free hemoglobin for use in the treatment of hemorrhagic shock comprising whole blood which has been treated by the method according to claim 1.

5. A stromal free hemoglobin solution prepared by the method of claim 2.

* * * * *